(12) United States Patent
Basa et al.

(10) Patent No.: US 10,213,370 B2
(45) Date of Patent: *Feb. 26, 2019

(54) DENTIFRICE COMPOSITIONS WITH IMPROVED FLUORIDE STABILITY

(71) Applicant: The Procter & Gamble Company, Cincinnati, OH (US)

(72) Inventors: Swapna Basa, Beijing (CN); James Albert Berta, West Chester, OH (US); Hongmei Yang, Beijing (CN); Ross Strand, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/347,821

(22) Filed: Nov. 10, 2016

(65) Prior Publication Data

US 2017/0135917 A1    May 18, 2017

(30) Foreign Application Priority Data

Nov. 13, 2015 (WO) .......................... CN2015094505

(51) Int. Cl.
  *A61Q 11/00* (2006.01)
  *A61K 8/21* (2006.01)
  *A61K 8/24* (2006.01)
  *A61K 6/00* (2006.01)
  *A61K 8/19* (2006.01)

(52) U.S. Cl.
  CPC .................. *A61K 8/21* (2013.01); *A61K 8/19* (2013.01); *A61K 8/24* (2013.01); *A61Q 11/00* (2013.01); *A61K 2800/52* (2013.01)

(58) Field of Classification Search
  CPC . A61Q 11/00; A61K 8/21; A61K 8/24; A61K 2800/48; A61K 2800/92
  See application file for complete search history.

(56) References Cited

U.S. PATENT DOCUMENTS

| | | | |
|---|---|---|---|
| 3,966,863 A | 6/1976 | Forward et al. | |
| 4,046,872 A | 9/1977 | Mitchell et al. | |
| 4,138,477 A | 2/1979 | Gaffar | |
| 4,144,322 A * | 3/1979 | Cordon .................. | A61K 8/25 424/49 |
| 4,283,385 A | 8/1981 | Dhabhar et al. | |
| 4,357,317 A | 11/1982 | Weyn et al. | |
| 4,425,323 A | 1/1984 | Morton et al. | |
| 4,482,536 A | 11/1984 | Hayes et al. | |
| 4,529,584 A | 7/1985 | Mulvey et al. | |
| 4,565,691 A | 1/1986 | Jackson | |
| 4,678,662 A | 7/1987 | Chan | |
| 4,701,319 A | 10/1987 | Woo | |
| 4,828,849 A | 5/1989 | Lynch et al. | |
| 6,106,811 A | 8/2000 | Gibbs | |
| 6,159,446 A | 12/2000 | Randive et al. | |
| 6,696,045 B2 | 2/2004 | Yue et al. | |
| 6,855,325 B1 | 2/2005 | Yvin et al. | |
| 8,007,771 B2 | 8/2011 | Ramji et al. | |
| 9,364,419 B2 | 6/2016 | Basa et al. | |
| 2002/0001569 A1 | 1/2002 | Dromard et al. | |
| 2002/0064504 A1 | 5/2002 | Kleinberg et al. | |
| 2003/0072721 A1 | 4/2003 | Riley et al. | |
| 2003/0157033 A1 | 8/2003 | Endo | |
| 2004/0120902 A1 | 6/2004 | Wernett et al. | |
| 2004/0131560 A1 | 7/2004 | Corcoran et al. | |
| 2006/0159631 A1 | 7/2006 | Buch et al. | |
| 2007/0053849 A1 | 3/2007 | Doyle et al. | |
| 2007/0166243 A1 | 7/2007 | Yoshida et al. | |
| 2007/0224134 A1 | 9/2007 | Regner et al. | |
| 2007/0231278 A1 | 10/2007 | Lee et al. | |
| 2009/0269287 A1 | 10/2009 | Berta | |
| 2009/0280072 A1 | 11/2009 | Shiba et al. | |
| 2010/0136069 A1 | 6/2010 | Deckner et al. | |
| 2010/0247589 A1 | 9/2010 | Fahnestock et al. | |
| 2010/0316580 A1 | 12/2010 | Kohli et al. | |
| 2012/0251466 A1* | 10/2012 | Pilch ........................ | A61K 8/21 424/52 |
| 2013/0022427 A1 | 1/2013 | Yamanaka et al. | |
| 2013/0064779 A1 | 3/2013 | Yamane et al. | |
| 2014/0127143 A1 | 5/2014 | Chandrasekaran | |
| 2014/0308321 A1 | 10/2014 | Midha et al. | |
| 2015/0050322 A1 | 2/2015 | Ashcroft et al. | |
| 2015/0352019 A1 | 4/2015 | Chen et al. | |
| 2015/0328089 A1 | 11/2015 | Chen et al. | |
| 2015/0328091 A1 | 11/2015 | Lei et al. | |
| 2015/0328093 A1 | 11/2015 | Chen et al. | |
| 2015/0328094 A1 | 11/2015 | Xu et al. | |
| 2015/0328105 A1 | 11/2015 | Strand et al. | |
| 2015/0328131 A1 | 11/2015 | Basa et al. | |
| 2016/0000667 A1 | 1/2016 | Potnis et al. | |
| 2016/0030326 A1 | 2/2016 | Basa et al. | |
| 2016/0250117 A1 | 9/2016 | Basa et al. | |
| 2016/0317406 A1 | 11/2016 | Chen et al. | |
| 2017/0014321 A1 | 1/2017 | D'Ambrogio et al. | |

FOREIGN PATENT DOCUMENTS

| | | |
|---|---|---|
| AU | 707998 | 7/1999 |
| EP | 0129201 A2 | 12/1984 |
| EP | 0333301 B1 | 10/1993 |
| GB | 1132830 | 11/1968 |
| GB | 2153673 | 2/1985 |
| GB | 2188548 | 4/1987 |
| KR | 20020054045 A | 7/2002 |
| KR | 2012042399 A | 5/2012 |
| WO | WO2002045678 A2 | 6/2002 |
| WO | WO2007107967 A1 | 9/2007 |
| WO | WO2007/122146 A1 | 11/2007 |
| WO | WO2009/134657 A1 | 11/2009 |
| WO | WO2016/172334 A1 | 10/2016 |

OTHER PUBLICATIONS

Pearce, E.I.F. et al., "The Effect of pH, Termperature and Plaque Thickness on the Hydrolysis of Monofluorophosphate in Experimental Dental Plaque", Caries Res Feb. 1, 2003; 37:178-184.

(Continued)

*Primary Examiner* — Tracy Liu

(74) *Attorney, Agent, or Firm* — Parker D. McCrary; James E. Oehlenschlager; Alexandra S. Anoff

(57) ABSTRACT

A dentifrice composition containing water, calcium-containing abrasive, fluoride ion source, and alkaline metal carbonate with improved fluoride stability.

18 Claims, No Drawings

(56) References Cited

OTHER PUBLICATIONS

Snorek et al. PQRI Recommendations on Particle-Size Analysis of Drug Substances Used in Oral Dosage Forms. Jun. 2007. J Pharm Sci. vol. 96. No. 6. pp. 1451-1467.
Ayad et al "Comparing the efficacy in reducing dentin hypersensitivity of a new toothpaste containing 8.0% arginine, calcium carbonate, and 1450 ppm fluoride to a commercial sensitive toothpaste containing 2% potassium ion: an eight-week clinical study on Canadian adults", Journal of Clinical Dentis, Professional Audience Communications, Yardley, PA, US, vo 1. 20, No. 1, Jan. 1, 2009 (Jan. 1, 2009), pp. 10-16.
Xu, Pengcheng, "Effect of arginine dentifrice on remineralization of initial enamel carious lesions" West China Journal of Stomatology, Feb. 28, 2014, No. 1, vol. 32.
PCT/CN2015/094504 International Search Report and Written Opinion dated Aug. 9, 2016.
PCT/CN2015/094504 Supplementary International Search Report and Written Opinion dated Dec. 13, 2017.
PCT/CN2015/094505 International Search Report and Written Opinion dated Nov. 13, 2015.
PCT/CN2015/094505 Supplementary International Search Report and Written Opinion dated Nov. 10, 2017.
PCT/CN2015/094506 International Search Report and Written Opinion dated Nov. 13, 2015.
PCT/CN2015/094506 Supplementary International Search Report and Written Opinion dated Oct. 20, 2017.
PCT/CN2015/094508 International Search Report and Written Opinion dated Nov. 13, 2015.
PCT/CN2015/094508 Supplementary International Search Report and Written Opinion dated Oct. 10, 2017.
PCT/CN2015/094514 International Search Report dated Nov. 13, 2015.
PCT/CN2015/094514 Supplementary International Search Report dated Oct. 10, 2017.
PCT/CN2015/094509 International Search Report dated Nov. 13, 2015.
PCT/CN2015/094509 Supplementary International Search Report dated Oct. 10, 2017.
All Office Actions, U.S. Appl. No. 15/347,823.
All Office Actions, U.S. Appl. No. 15/347,824.
All Office Actions, U.S. Appl. No. 15/347,897.
All Office Actions, U.S. Appl. No. 15/347,830.
All Office Actions, U.S. Appl. No. 15/347,837.
All Office Actions, U.S. Appl. No. 15/347,840.

* cited by examiner

DENTIFRICE COMPOSITIONS WITH IMPROVED FLUORIDE STABILITY

FIELD OF THE INVENTION

The present invention relates to dentifrice compositions having high water and high carbonate levels and a fluoride ion source.

BACKGROUND OF THE INVENTION

Dentifrice compositions are well known for dental and oral hygiene care. High water (e.g., >44 wt %) and high carbonate (e.g., >24 wt %) formulation chassis are a cost effective for many markets and consumers. However, this formulation chassis sometimes has fluoride ion stability issues that often exacerbated when there are high temperatures and/or long distribution times such as in some developing markets. Fluoride, and its associated benefits in dentifrice composition, is critical for a user's experience and product acceptance. There is a need to provide such dentifrice formulations having improved fluoride ion stability.

SUMMARY OF THE INVENTION

The present invention is based, in part, on the surprising observation that in high water and high carbonate dentifrice formulations, sodium carbonate has an important impact in fluoride stability. Furthermore, this fluoride ion stability effect is further enhanced at pH conditions that are greater than pH 8.0. The pH is preferably buffered with phosphate-based pH buffering agents.

Accordingly, an advantage of the present invention is improved soluble fluoride stability over time (in the high water high carbonate dentifrice formulation claimed herein).

One aspect of the invention provides for a dentifrice composition comprising: (a) 45% to 75%, by weight of the composition, of water; (b) 25% to 50%, by weight of the composition, of a calcium-containing abrasive; (c) 0.0025% to 2%, by weight of the composition, of a fluoride ion source; (d) greater than 0.3%, by weight of the composition, of alkaline metal carbonate; and a pH greater than 8. Preferably the alkaline metal carbonate comprises from 0.4% to 2%, preferably from 0.5% to 1.8%, more preferably from 0.6% to 1.5%, yet more preferably from 0.7% to 1.3%, by weight of the composition. Preferably the alkaline metal carbonate is sodium carbonate. More preferably the composition further comprises a pH modifying agent, wherein the pH modifying agent is an alkali metal phosphate, preferably the alkali metal phosphate comprises from 0.001% to 3% by weight of the composition, more preferably the alkali metal phosphate is selected from the group consisting of monosodium phosphate, trisodium phosphate, and combinations thereof. Preferably the dentifrice composition is a single phase composition.

Another aspect of the invention provides for a dentifrice composition comprising:
(a) 45% to 75%, by weight of the composition, of water; (b) 25% to 50%, by weight of the composition, of a calcium-containing abrasive; (c) 0.0025% to 2%, by weight of the composition, of a fluoride ion source; (d) an alkaline metal carbonate; (e) a pH modifying agent, wherein the pH modifying agent is an alkali metal phosphate, wherein the alkali metal phosphate comprises from 0.001% to 3% by weight of the composition; and a pH greater than 8. Preferably the alkaline metal carbonate is sodium carbonate.

Another aspect of the invention provides for a method of treating tooth enamel comprising the step of brushing teeth with the aforementioned dentifrice composition.

While the specification concludes with claims that particularly point out and distinctly claim the invention, it is believed the present invention will be better understood from the following description.

DETAILED DESCRIPTION OF THE INVENTION

Definitions

The term "comprising" as used herein means that steps and ingredients other than those specifically mentioned can be added. This term encompasses the terms "consisting of" and "consisting essentially of." The compositions of the present invention can comprise, consist of, and consist essentially of the essential elements and limitations of the invention described herein, as well as any of the additional or optional ingredients, components, steps, or limitations described herein.

The term "dentifrice" as used herein means paste, gel, powder, tablets, or liquid formulations, unless otherwise specified, that are used to clean the surfaces of the oral cavity. Preferably the dentifrice compositions of the present invention are single phase compositions. The term "teeth" as used herein refers to natural teeth as well as artificial teeth or dental prosthesis.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified. The term "weight percent" may be denoted as "wt %" herein.

As used herein, the articles including "a" and "an" when used in a claim, are understood to mean one or more of what is claimed or described.

As used herein, the terms "comprise", "comprises", "comprising", "include", "includes", "including", "contain", "contains", and "containing" are meant to be non-limiting, i.e., other steps and other sections which do not affect the end of result can be added. The above terms encompass the terms "consisting of" and "consisting essentially of".

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

Calcium-Containing Abrasive

The compositions of the present invention comprise from 25% to 50% by weight of a calcium-containing abrasive, wherein preferably the calcium-containing abrasive is selected from the group consisting of calcium carbonate, calcium glycerophosphate, dicalcium phosphate, tricalcium phosphate, calcium orthophosphate, calcium metaphosphate, calcium polyphosphate, calcium oxyapatite, and combinations thereof, wherein more preferably the calcium-containing abrasive is calcium carbonate. In preferred embodiment, the calcium carbonate is 27% to 47%, preferably 27% to 37%, more preferably from 28% to 34%, yet still more preferably from 29% to 33%, by weight of the composition. More preferably, the calcium-containing abrasive is selected from the group consisting of ground calcium carbonate, precipitated calcium carbonate, and combinations thereof. Fine ground natural chalk (FGNC) is one of the more preferred calcium-containing abrasives useful in the present invention. It is obtained from limestone or marble. FGNC may also be modified chemically or physically by coating during milling or after milling by heat treatment. Typical coating materials include magnesium stearate or oleate. The morphology of FGNC may also be modified during the milling process by using different milling techniques, for example, ball milling, air-classifier milling or spiral jet milling. One example of natural chalk is described in WO 03/030850 having a medium particle size of 1 to 15 µm and a BET surface area of 0.5 to 3 $m^2/g$. The natural calcium carbonate may have a particle size of 325 to 800 mesh, alternatively a mess selected from 325, 400 600, 800, or combinations thereof; alternatively the particle size is from 0.1 to 30 microns, or from 0.1 to 20 microns, or from 5 to 20 microns.

Water

The dentifrice compositions of the present invention comprise herein from 45% to 75%, by weight of the composition, of water. Preferably the dentifrice composition comprises from 45% to 70%, more preferably from 45% to 60%, alternatively from 50% to 60%, alternatively from 52% to 60%, by weight of the composition, of water. The water may be added to the formulation and/or may come into the composition from the inclusion of other ingredients. Preferably the water is USP water.

Fluoride Ion Source

The compositions may include an effective amount of an anti-caries agent. In one embodiment, the anti-caries agent is a fluoride ion source. The fluoride ion may be present in an amount sufficient to give a fluoride ion concentration in the composition at 25° C., and/or in one embodiment can be used at levels of from 0.0025% to 5% by weight of the composition, alternatively from 0.005% to 2.0% by weight of the composition, to provide anti-caries effectiveness. Representative fluoride ion sources include: stannous fluoride, sodium fluoride, potassium fluoride, amine fluoride, sodium monofluorophosphate, and zinc fluoride. In one embodiment the dentifrice composition contains a fluoride source selected from stannous fluoride, sodium fluoride, and mixtures thereof. In one embodiment, the fluoride ion source is sodium monofluorophosphate, and wherein the composition comprises 0.0025% to 2%, by weight of the composition, of the sodium monofluorophosphate, alternatively from 0.5% to 1.5%, alternatively from 0.6% to 1.7%, alternatively combinations thereof. In another embodiment, the composition comprises from 0.0025% to 2%, by weight of the composition, of a fluoride ion source. In one example, the dentifrice compositions of the present invention may have a dual fluoride ion source, specifically sodium monofluorophosphate and an alkaline metal fluoride. Such an approach may provide an improvement in mean fluoride update.

pH

The pH of the dentifrice composition may be greater than pH 8.0, preferably from greater than pH 8 to pH 12. Preferably the pH is greater than 8.1, more preferably the pH is greater than pH 8.5, even more preferably the pH is greater than pH 9, alternatively the pH is from pH 9.0 to pH 10.5, alternatively from pH 9 to pH 10. The relatively high pH of the present inventive composition may help fluoride stability. Without wishing to be bound by theory, at below pH 8, calcium ion may bind with the fluoride. Thus it is desirable to have the dentifrice composition have a greater than pH 8.0 to maximize the stability of the fluoride ion source. A method for assessing pH of dentifrice is described is provided in the analytical methods section provided below. For purposes of clarification, although the analytical method describes testing the dentifrice composition when freshly prepared, for purposes of claiming the present invention, the pH may be taken at anytime during the product's reasonable lifecycle (including but not limited to the time the product is purchased from a store and brought to the consumer's home).

Alkaline Metal Carbonate

The present invention is based, in part, on the surprising observation that in high water, high carbonate, alkaline pH, dentifrice formulations having an alkaline metal carbonate (e.g., sodium carbonate) and at levels greater than 0.3 wt %, has an important impact in fluoride stability. Alternatively, the invention is based, in part on the surprising observation that in high water, high carbonate, alkaline pH, dentifrice formulations having an alkaline metal carbonate (e.g., sodium carbonate) and a pH modifying agent (wherein the pH modifying agent is an alkali metal phosphate, wherein the alkali metal phosphate comprises from 0.001% to 3% by weight of the composition) has an important impact in fluoride stability.

Preferably the alkaline metal carbonate is selected from sodium carbonate, potassium carbonate, or combination thereof, more preferably the alkaline metal carbonate is sodium carbonate Preferably the dentifrice composition herein comprises from 0.4% to 2%, by weight of the composition, of alkaline metal carbonate. More preferably the composition comprises from 0.5% to 1.8%, yet more preferably from 0.6% to 1.5%, yet still more preferably from 0.7% to 1.3%, by weight of the composition of the s alkaline metal carbonate. In one example, the composition contains 1%, by weight of the composition, of sodium carbonate. Without wishing to be bound by theory, higher levels of alkaline metal carbonate may provide challenges in maintaining the pH of the dentifrice compositions and having pH buffering systems with enough buffering capacity to keep the pH at preferred ranges (as indicated above). Again, without wishing to be bound by theory, these pH ranges may have in impact on long term impact of fluoride ion stability, especially wherein the fluoride ion source is sodium monofluorophosphate.

pH Modifying Agent

The dentifrice compositions herein may include an effective amount of a pH modifying agent, alternatively wherein the pH modifying agent is a pH buffering agent. pH modifying agents, as used herein, refer to agents that can be used to adjust the pH of the dentifrice compositions to the above-identified pH range. pH modifying agents may include alkali metal hydroxides, ammonium hydroxide, organic ammonium compounds, carbonates, sesquicarbonates, borates, silicates, phosphates, imidazole, and mixtures thereof. A preferred pH modifying agent is an alkali metal phosphate, more preferably the dentifrice composition comprises from 0.001% to 3%, by weight of the composition, of one or more the alkali metal phosphates. In turn, preferred alkali metal phosphates include monosodium phosphate (monobasic sodium phosphate or "MSP"), trisodium phosphate (sodium phosphate tribasic dodecahydrate or "TSP"), and combination thereof. More preferably the composition comprises 0.01% to 3%, preferably from 0.1% to 1%, more preferably from 0.2% to 0.8%, by weight of the composition, of TSP. More preferably the composition comprises 0.001% to 2%, preferably from 0.01% to 0.3%, alternatively from 0% to less than 0.42%, alternatively from 0.001% to 0.2%, by weight of the composition, of MSP is used.

Without wishing to be bound by theory, TSP and MSP may also have calcium ion chelating activity and therefore provide some monofluorophosphate stabilization (in those formulations containing monofluorophosphate).

Other pH agents include sodium benzoate, benzoic acid, sodium hydroxide, potassium hydroxide, imidazole, sodium gluconate, lactic acid, sodium lactate, citric acid, sodium citrate, phosphoric acid.

Thickening System

The dentifrice compositions of the present invention may comprise a thickening system. Preferably the dentifrice composition comprises from 0.5% to 4%, preferably from 0.8% to 3.5%, more preferably from 1% to 3%, yet still more preferably from 1.3% to 2.6%, by weight of the composition, of the thickening system. More preferably the thickening system comprises a thickening polymer, a thickening silica, or a combination thereof. Yet more preferably, when the thickening system comprises a thickening polymer, the thickening polymer is selected from a carboxymethyl cellulose, a linear sulfated polysaccharide, a natural gum, and combinations thereof. Yet still more preferably, when the thickening system comprises a thickening polymer, the thickening polymer is selected from the group consisting of: (a) 0.01% to 3% of a carboxymethyl cellulose ("CMC") by weight of the composition, preferably 0.1% to 2.5%, more preferably 0.2% to 1.5%, by weight of the composition, of CMC; (b) 0.01% to 2.5%, preferably 0.05% to 2%, more preferably 0.1% to 1.5%, by weight of the composition, of a linear sulfated polysaccharide, preferably wherein the linear sulfated polysaccharide is a carrageenan; (c) 0.01% to 7%, preferably 0.1% to 4%, more preferably from 0.1% to 2%, yet more preferably from 0.2% to 1.8%, by weight of the composition, of a natural gum; (d) combinations thereof. Preferably when the thickening system comprises a thickening silica, the thickening silica is from 0.01% to 10%, more preferably from 0.1% to 9%, yet more preferably 1% to 8% by weight of the composition.

Preferably the linear sulfated polysaccharide is a carrageenan (also known as carrageenin). Examples of carrageenan include Kappa-carrageenan, Iota-carrageenan, Lambda-carrageenan, and combinations thereof.

In one example the thickening silica is obtained from sodium silicate solution by destabilizing with acid as to yield very fine particles. One commercially available example is ZEODENT® branded silicas from Huber Engineered Materials (e.g., ZEODENT® 103, 124, 113 115, 163, 165, 167).

In one example the CMC is prepared from cellulose by treatment with alkali and monochloro-acetic acid or its sodium salt. Different varieties are commercially characterized by viscosity. One commercially available example is Aqualon™ branded CMC from Ashland Special Ingredients (e.g., Aqualon™ 7H3SF; Aqualon™ 9M3SF Aqualon™ TM9A; Aqualon™ TM12A).

Preferably a natural gum is selected from the group consisting of gum karaya, gum arabic (also known as acacia gum), gum tragacanth, xanthan gum, and combination thereof. More preferably the natural gum is xanthan gum. Xanthan gum is a polysaccharide secreted by the bacterium Xanthomonas camestris. Generally, xanthan gum is composed of a pentasaccharide repeat units, comprising glucose, mannose, and glucuronic acid in a molar ratio of 2:2:1, respectively. The chemical formula (of the monomer) is $C_{35}H_{49}O_{29}$. In one example, the xanthan gum is from CP Kelco Inc (Okmulgee, US).

PEG

The compositions of the present invention may comprise polyethylene glycol (PEG), of various weight percentages of the composition as well as various ranges of average molecular weights. In one aspect of the invention, the compositions have from 0.01% to 8%, preferably from 0.1% to 5%, more preferably from 0.2% to 4.8%, yet more preferably from 0.3% to 4.2%, yet still more preferably from 0.5% to 4%, by weight of the composition, of PEG. In another aspect of the invention, the PEG is one having a range of average molecular weight from 100 Daltons to 1600 Daltons, preferably from 200 to 1000, alternatively from 400 to 800, alternatively from 500 to 700 Daltons, alternatively combinations thereof. PEG is a water soluble linear polymer formed by the addition reaction of ethylene oxide to an ethylene glycol equivalent having the general formula : $H-(OCH_2CH_2)_n-OH$. One supplier of PEG is Dow Chemical Company under the brandname of CARBOWAX™. Without wishing to be bound by theory, having some PEG in the dentifrice composition may help with physical stability.

Anti-Calculus Agent

The dentifrice compositions may include an effective amount of an anti-calculus agent, which in one embodiment may be present from 0.05% to 50%, by weight of the composition, alternatively from 0.05% to 25%, alternatively from 0.1% to 15% by weight of the composition. Non-limiting examples include those described in US 2011/0104081 A1 at paragraph 64, and those described in US 2012/0014883 A1 at paragraphs 63 to 68, as well as the references cited therein. One example is a pyrophosphate salt as a source of pyrophosphate ion. In one embodiment, the composition comprises tetrasodium pyrophosphate (TSPP) or disodium pyrophosphate or combinations thereof, preferably 0.01% to 2%, more preferably from 0.1% to 1%, by weight of the composition, of the pyrophosphate salt. Without wishing to be bound by theory, TSPP may provide not only calcium chelating thereby mitigating plaque formation, but may also provide the additional benefit of monofluorophosphate stabilization (in those formulations containing monofluorophosphate).

Surfactant

The dentifrice compositions herein may include a surfactant. The surfactant may be selected from anionic, nonionic, amphoteric, zwitterionic, cationic surfactants, or mixtures thereof. The composition may include a surfactant at a level of from 0.1% to 10%, from 0.025% to 9%, from 0.05% to 5%, from 0.1% to 2.5%, from 0.5% to 2%, or from 0.1% to 1% by weight of the total composition. Non-limiting examples of anionic surfactants may include those described at US 2012/0082630 A1 at paragraphs 32, 33, 34, and 35. Non-limiting examples of zwitterionic or amphoteric surfactants may include those described at US 2012/0082630 A1 at paragraph 36; cationic surfactants may include those described at paragraphs 37 of the reference; and nonionic surfactants may include those described at paragraph 38 of the reference. In one embodiment the composition comprises 0.1% to 5%, preferably 0.1% to 3%, alternatively from 0.3% to 3%, alternatively from 1.2% to 2.4%, alternatively from 1.2% to 1.8%, alternatively from 1.5% to 1.8%, by weight of the composition, alternatively combinations thereof, of the anionic surfactant sodium lauryl sulfate (SLS).

Preferably the dentifrice compositions of the present invention comprise from 0.1% to 12%, by weight of the composition, of a surfactant, more preferably 1% to 9% of the surfactant, yet more preferably wherein the surfactant is an anionic surfactant, yet still more preferably wherein the anionic surfactant is sodium lauryl sulfate.

Low or Free Humectants

The compositions herein may be substantially free or free of humectants, alternatively contain low levels of humectants. The term "humectant," for the purposes of present invention, include edible polyhydric alcohols such as glycerin, sorbitol, xylitol, butylene glycol, propylene glycol, and combinations thereof. In one embodiment, the humectant is a polyol, preferably wherein the polyol is selected from sorbitol, glycerin, and combinations thereof. In yet another embodiment, the humectant is sorbitol. In one embodiment, the composition comprises from 0% to less than 5%, by weight of the composition, of humectants, preferably from 0% to 4%, alternatively from 0% to 3%, alternatively from 0% to 2%, alternatively from 0% to 1%, by weight of th4 composition, of humectants. A potential advantage of having a dentifrice composition that is free or substantially free of humectants is, without wishing to be bound by theory, is those dentifrice compositions that are free of polyols (e.g., glycerin and sorbitol), or have a relatively low amount thereof, may provide better fluoride uptake compared to those compositions having the high levels of such polyols (or humectants for that matter). In one example, the dentifrice compositions of the present invention comprise from 0% to 5%, preferably 0% to 3%, more preferably 0% to 1%, by weight of the composition, of glycerin, sorbitol, or combinations thereof; yet more preferably the composition is substantially free of both glycerin and sorbitol.

Sweetener

The oral care compositions herein may include a sweetening agent. These sweetener agents may include saccharin, dextrose, sucrose, lactose, maltose, levulose, aspartame, sodium cyclamate, D-tryptophan, dihydrochalcones, acesulfame, sucralose, neotame, and mixtures thereof. Sweetening agents are generally used in oral compositions at levels of from 0.005% to 5%, by weight of the composition, alternatively 0.01% to 1%, alternatively from 0.1% to 0.5%, alternatively combinations thereof.

Colorant

The compositions herein may include a colorant. Titanium dioxide is one example of a colorant. Titanium dioxide is a white powder which adds opacity to the compositions. Titanium dioxide generally can comprise from 0.25% to 5%, by weight of the composition.

Flavorant

The compositions herein may include from 0.001% to 5%, alternatively from 0.01% to 4%, alternatively from 0.1% to 3%, alternatively from 0.5% to 2%, alternatively 1% to 1.5%, alternatively 0.5% to 1%, by weight of the composition, alternatively combinations thereof, of a flavorant composition. The term flavorant composition is used in the broadest sense to include flavor ingredients, or sensates, or sensate agents, or combinations thereof. Flavor ingredients may include those described in US 2012/0082630 A1 at paragraph 39; and sensates and sensate ingredients may include those described at paragraphs 40-45, incorporated herein by reference. Excluded from the definition of flavorant composition is "sweetener" (as described above).

Viscosity

A viscosity of 150000 cP to 850000 cP is a classic viscosity target range for a consumer acceptable dentifrice. The compositions of the present invention are preferably within this range. A method for assessing viscosity is described. The viscometer is Brookfield® viscometer, Model DV-I Prime with a Brookfield "Helipath" stand. The viscometer is placed on the Helipath stand and leveled via spirit levels. The E spindle is attached, and the viscometer is set to 2.5 RPM. Detach the spindle, zero the viscometer and install the E spindle. Then, lower the spindle until the crosspiece is partially submerged in the paste before starting the measurement. Simultaneously turn on the power switch on the viscometer and the helipath to start rotation of the spindle downward. Set a timer for 48 seconds and turn the timer on at the same time as the motor and helipath. Take a reading after the 48 seconds. The reading is in cP.

Preferably the dentifrice compositions of the present invention are characterized as having viscosity from 150,000 cP to 850,000 cP as measured according to the method described herein, more preferably the dentifrice composition is a single phase composition.

Phase Stability

The term "phase stability" means visually (i.e., to the unaided eye) having no liquid separated from the oral care composition (e.g., toothpaste) body over a defined period of time under ambient conditions. In other words, a phase stable composition will resist syneresis. The compositions of the present invention are preferably phase stable for at least 6 months, more preferably 12 months or more.

EXAMPLES

Analytical Methods

The method for assessing soluble fluoride is described consistent with the China's National Standard Method GB8372-2008. Briefly, an ion-selective electrode (ISE) is used to test soluble fluoride in dentifrice. An example of a fluoride ion meter is SARTORIUS PP-50, but an equivalent may be used. The ion meter may be fitted with a fluoride-specific ion electrode with a single-junction reference electrode by Orion Research Inc., Cat. No. 9609BNWP, but an equivalent may be used. The sample is prepared by using a balance that is accurate to the 0.0001 gram (g). 20 g of dentifrice is weighed into a tarred 50 mL plastic beaker and then gradually 50 mL of deionized water is added, while a magnetic stir bar is stirring in the plastic beaker, until the dentifrice is a completely disperse solution. The entire solution is gently transferred to a 100mL plastic volumetric flask as to avoid generating foam (so the volume can be measured accurately), and deionized water is added to reach a total volume 100 ml, and then the solution is shaken manually to form a slurry. The formed slurry is then transferred into 10 mL centrifuge tubes, and centrifued for 10 minutes at 15000 rotations-per-minute (RPM) (at 24149 g force) at ambient temperature. Thereafter 0.5 mL of supernatant is transferred into a 2 mL mini-centrifugal tube, and 0.7 mL of 4 mol/L HCl is added to the tub. Then the tub is capped, heated in a 50° C. waterbath for 10 minutes. Thereafter the contents of the tub are transferred to a 50 mL measuring flask. The following are also added to the flask: 0.7 mL of 4 mol/L NaOH to neutralize the solution; 5 mL of citrate buffer solution (described further below); deionized water is added until a total volume of 50 mL is achieved in the flask; and then the sample solution is gently mixed. The aforementioned citrate buffer solution is prepared by dissolving 100 g of sodium citrate, 60 mL of glacial acetic acid, 60 g of NaCl, and 30g of NaOH, all with water, adjusting the pH to 5.0~5.5, and diluting the citrate buffer solution with deionized water until a total volume of 1000 mL is achieved. Turning back to the sample solution, the entire 50 mL solution is transferred to a 50 mL plastic beaker and the fluoride level is assessed based on a fluoride standard curve using the fluoride ion meter and electrode described.

The standard fluoride curve (w/w %) is prepared by accurately measuring 0.5 mL, 1.0 mL, 1.5 mL, 2.0 mL, and 2.5 mL fluoride ion standard solutions (100 mg/kg) into five respective 50 mL plastic measuring flasks. 5mL of citrate buffer solution (made as previously described above) into each respective flask, and then diluting each solution to the scale with deionized water. Thereafter, each solution is transferred into a 50 mL plastic beaker respectively, measuring potential E under magnetic agitation, recording potential values, and drawing E-logc (wherein "c" is a concentration) standard curve.

A method for assessing pH of dentifrice is described. pH is measured by a pH Meter with Automatic Temperature Compensating (ATC) probe. The pH Meter is capable of reading to 0.001 pH unit. The pH electrode may be selected from one of the following (i) Orion Ross Sure-Flow combination: Glass body—VWR #34104-834/Orion #8172BN or VWR #10010-772/Orion #8172BNWP; Epoxy body—VWR #34104-830/Orion #8165BN or VWR #10010-770/Orion #8165BNWP; Semi-micro, epoxy body—VWR #34104-837/Orion #8175BN or VWR #10010-774/Orion #3175BNWP; or (ii) Orion PerpHect combination: VWR #34104-843/Orion #8203BN semi-micro, glass body; or (iii) suitable equivalent. The automatic temperature compensating probe is Fisher Scientific, Cat #13-620-16.

A 25% by weight slurry of dentifrice is prepared with deionized water, and thereafter is centrifuged for 10 minutes at 15000 rotations-per-minute using a SORVALL RC 28S centrifuge and SS-34 rotor (or equivalent gravitational force, at 24149g force). The pH is assessed in supernatant after one minute. After each pH assessment, the electrode is washed with deionized water. Any excess water is wiped with a laboratory grade tissue. When not in issue, the electrode is kept immersed in a pH 7 buffer solution or an appropriate electrode storage solution.

Compositional Components

Table 1 provides compositional components of inventive examples 4-5, and comparative examples 1-3, 6-8. Notably, the inventive compositions contain sodium carbonate whereas the comparative compositions do not.

TABLE 1

Composition components of dentifrice compositions of examples 1-8.

| Components: (Wt %) | Ex 1 | Ex 2 | Ex 3 | Ex 4 | Ex 5 | Ex 6 | Ex 7 | Ex 8 |
|---|---|---|---|---|---|---|---|---|
| Comparative = C Inventive = I | C | C | C | I | I | C | C | C |
| Sodium Carbonate | 0 | 0 | 0 | 0.5 | 1 | 0.3 | 0 | 0 |
| Mono Sodium Phosphate (MSP) | 0 | 0.08 | 0.15 | 0.17 | 0.55 | 0 | 0 | 0 |
| Sodium Triphosphate (TSP) | 0.52 | 0.42 | 0.40 | 0.38 | 0 | 0 | 0 | 0 |
| Water | 56.00 | 55.52 | 54.97 | 55.47 | 54.97 | 57.32 | 56.72 | 57.62 |
| Calcium Carbonate | 32 | 32 | 32 | 32 | 32 | 32 | 32 | 32 |
| Sodium Monofluorophosphate | 1.1 | 1.1 | 1.1 | 1.1 | 1.1 | 1.1 | 1.1 | 1.1 |
| Tetra Sodium Pyrophosphate | 0 | 0.5 | 1 | 0 | 0 | 0 | 0.9 | 0 |
| Carrageenan | 0 | 0.4 | 0.8 | 1.3 | 2 | 1 | 2 | 3 |
| Sodium Carboxymethyl Cellulose | 0.91 | 0.91 | 0.91 | 0.91 | 0.91 | 0.91 | 0.91 | 0.91 |
| Thickening Silica | 2.62 | 2.62 | 2.62 | 2.62 | 2.62 | 2.62 | 2.62 | 2.62 |
| Sodium Saccharine | 0.58 | 0.58 | 0.58 | 0.58 | 0.58 | 0.58 | 0.58 | 0.58 |
| Sodium Lauryl Sulfate | 4 | 4 | 4 | 4 | 4 | 4 | 4 | 4 |
| Flavor | 0.85 | 0.85 | 0.85 | 0.85 | 0.85 | 0.85 | 0.85 | 0.85 |
| Sodium hydroxide | 0 | 0 | 0 | 0 | 0 | 0 | 0 | 0.16 |
| Total: | 100 | 100 | 100 | 100 | 100 | 100 | 100 | 100 |
| Initial pH: | 9.13 | 9.39 | 9.59 | 9.64 | 9.51 | 9.37 | 9.5 | 9.27 |

Data

Fluoride stability and pH change of the eight examples are provided in Tables 2a and 2b. The amount of soluble fluoride and pH, at weeks 0, 26, 52, 78, 104, and finally after two years, at 30° C., is measured according to the analytical methods above. Table 2c provides the fluoride loss after two years at 30° C. for the subject examples.

Soluble fluoride is provided as parts per million ("ppm"). The compositional components of these examples are described in earlier Table 1.

TABLE 2a

Fluoride Stability Profile at 30° C. Two Years.

| | Example 1 | | Example 2 | | Example 3 | | Example 4 (Inventive) | |
|---|---|---|---|---|---|---|---|---|
| Weeks: | Soluble Fluoride (ppm) | pH | Soluble Fluoride (ppm) | pH | Soluble Fluoride (ppm) | pH | Soluble Fluoride (ppm) | pH |
| 0 | 1100 | 9.13 | 1160 | 9.39 | 1318 | 9.59 | 1326 | 9.64 |
| 26 | 1116 | 8.62 | 1132 | 8.86 | 1300 | 9.37 | 1300 | 9.45 |
| 52 | 1012 | 8.58 | 912 | 8.92 | 1200 | 9.2 | 1300 | 9.36 |

TABLE 2a-continued

Fluoride Stability Profile at 30° C. Two Years.

| Weeks: | Example 1 | | Example 2 | | Example 3 | | Example 4 (Inventive) | |
|---|---|---|---|---|---|---|---|---|
| | Soluble Fluoride (ppm) | pH | Soluble Fluoride (ppm) | pH | Soluble Fluoride (ppm) | pH | Soluble Fluoride (ppm) | pH |
| 78 | 848 | 8.54 | 730 | 8.86 | 889 | 9.11 | 1170 | 9.14 |
| 104 | 636 | 8.52 | 592 | 8.91 | 936 | 9.13 | 1128 | 9.09 |

TABLE 2b

Fluoride Stability Profile at 30° C. Two Years

| Weeks: | Example 5 (Inventive) | | Example 6 | | Example 7 | | Example 8 | |
|---|---|---|---|---|---|---|---|---|
| | Soluble Fluoride (ppm)) | pH | Soluble Fluoride (ppm)) | pH | Soluble Fluoride (ppm) | pH | Soluble Fluoride (ppm) | pH |
| 0 | 1200 | 9.51 | 1306 | 9.37 | 1332 | 9.5 | 1299 | 9.27 |
| 26 | 1300 | 9.4 | 1200 | 8.85 | 1300 | 9.1 | 1100 | 8.58 |
| 52 | 1300 | 9.28 | 1100 | 8.69 | 1300 | 8.96 | 1000 | 8.62 |
| 78 | 1266 | 9.18 | 678 | 8.64 | 840 | 8.42 | 698 | 8.84 |
| 104 | 1142 | 9.08 | 864 | 8.7 | 848 | 8.87 | 656 | 8.51 |

| | Ex 1 | Ex 2 | Ex 3 | Ex 4 (Inventive) | Ex 5 (Inventive) | Ex 6 | Ex 7 | Ex 8 |
|---|---|---|---|---|---|---|---|---|
| Total Soluble Fluoride Loss After 104 weeks | 464 | 568 | 382 | 198 | 58 | 442 | 484 | 643 |

There are a number of observations that can be obtained from the data of Tables 2a, 2b and 2c. Firstly, inventive examples 4 and 5 demonstrate the least amount of soluble fluoride loss over the course of the study (i.e., lowest level of soluble fluoride loss) as compared to the comparative examples (1-3 and 6-8). Between the inventive examples, example 5 has the least amount of fluoride loss at 58 parts per million (ppm) while containing the greatest amount of sodium carbonate (at 1 wt %). The second best performing dentifrice composition is inventive example 4, notably containing 0.5 wt % sodium carbonate, demonstrating a soluble fluoride loss of only 198 ppm. Both inventive examples 4 and 5 contain the pH buffering agent monosodium phosphate (monobasic sodium phosphate or "MSP") at 0.17 wt % and 0.55 wt %, respectively. Example 4 also contains the pH buffering agent trisodium phosphate (sodium phosphate tribasic dodecahydrate or "TSP"). Comparative example 6 contains a relatively low level of sodium carbonate at 0.3 wt %, but contains neither MSP or TSP and has a soluble fluoride loss of 382 ppm. Comparative example 3 does not contain any sodium carbonate but contains both MSP and TSP at 0.15 wt % and 0.4 wt %, respectively, and with a total fluoride loss of 384. Clearly, the inventive compositions (containing greater than 0.3 wt % sodium carbonate) provide superior results over comparative examples 3 and 6, but interestingly example 3 ostensibly demonstrates an improvement over example 6 despite not having any sodium carbonate. Therefore, there is a suggestion of synergy between the use of sodium carbonate and the alkali metal phosphate pH buffering agents MSP and/or TSP.

Examples 7 and 8 notably do not contain any MSP, TSP, or sodium carbonate; and provides results less favorable than the inventive examples. Example 7 contains Tetra Sodium Pyrophosphate and while Example 8 uses sodium hydroxide to adjust the pH. Examples 1 and 2 do not contain sodium carbonate, but both contain TSP. Example 2 also contains MSP. Both examples 1 and 2 have results less favorable than the inventive examples.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dentifrice composition comprising:
   (a) 45% to 75%, by weight of the composition, of water;
   (b) 25% to 50%, by weight of the composition, of a calcium-containing abrasive;
   (c) 0.0025% to 2%, by weight of the composition, of a fluoride ion source;
   (d) greater than 0.3%, by weight of the composition, of alkaline metal carbonate;
   (e) from 0.001% to 3%, by weight of the composition, of an alkali metal phosphate; and
   (f) a pH greater than 9.

2. The dentifrice composition according to claim 1, wherein the alkali metal phosphate is selected from the group consisting of monosodium phosphate, trisodium phosphate, and combinations thereof.

3. The dentifrice composition according to claim 2, wherein the alkali metal phosphate comprises from 0.01% to 3%, by weight of the composition, monosodium phosphate.

4. The dentifrice composition according to claim 1, wherein the alkaline metal carbonate is selected from the group consisting of sodium carbonate, potassium carbonate, or combination thereof.

5. The dentifrice composition according to claim 4, wherein the alkaline metal carbonate comprises sodium carbonate.

6. The dentifrice composition according to claim 4, wherein the composition comprises from 0.5% to 1.8%, by weight of the composition, alkaline metal carbonate.

7. The dentifrice composition according to claim 1, wherein the calcium-containing abrasive comprises 27% to 47%, by weight, calcium carbonate.

8. The dentifrice composition according to claim 1, wherein the fluoride ion source comprises 0.5% to 1.5%, sodium monofluorophosphate.

9. The dentifrice composition according to claim 1, comprising from 50% to 60%, by weight of the composition, water.

10. The dentifrice composition according to claim 1, further comprising a thickening system, wherein the thickening system is selected from the group consisting of a thickening polymer, a thickening silica, and combinations thereof.

11. The dentifrice composition according to claim 10, wherein the thickening system comprises a thickening polymer wherein the thickening polymer is selected from the group consisting of carboxymethyl cellulose, linear sulfated polysaccharide, natural gum, and combinations thereof.

12. The dentifrice composition according to claim 10, wherein the thickening system comprises a thickening polymer wherein the thickening polymer comprises from 0.01% to 3%, by weight of the composition, carboxymethyl cellulose.

13. The dentifrice composition according to claim 10, wherein the thickening system comprises a thickening polymer wherein the thickening polymer comprises from 0.01% to 2.5%, by weight of the composition, linear sulfated polysaccharide.

14. The dentifrice composition according to claim 13, wherein the linear sulfated polysaccharide comprises carrageenan.

15. The dentifrice composition according to claim 10, wherein the thickening system comprises a thickening polymer wherein the thickening polymer comprises from 0.01% to 7%, by weight of the composition, natural gum.

16. The dentifrice composition according to claim 10, wherein the thickening system comprises from 0.01% to 10%, by weight of the composition, thickening silica.

17. The dentifrice composition according to claim 10, wherein the composition comprises from 0.5% to 4%, by weight, thickening system.

18. A dentifrice composition comprising:
   (a) 45% to 75%, by weight of the composition, of water;
   (b) 25% to 50%, by weight of the composition, of a calcium-containing abrasive;
   (c) 0.0025% to 2%, by weight of the composition, of a fluoride ion source;
   (d) greater than 0.3% by weight of the composition, of an alkaline metal carbonate;
   (e) from 0.001% to 3%, by weight of the composition, of an alkali metal phosphate,
   (f) a pH greater than 8; and
   wherein the composition is free of a humectant selected from sorbitol, glycerin, and combinations thereof.

* * * * *